(12) United States Patent
Xu et al.

(10) Patent No.: US 11,944,384 B2
(45) Date of Patent: Apr. 2, 2024

(54) PREOPERATIVE PLANNING METHOD FOR MULTIMODAL ABLATION TREATMENT AND APPARATUS THEREOF

(71) Applicants: Xuemin Xu, Shanghai (CN); Aili Zhang, Shanghai (CN); Jianqi Sun, Shanghai (CN); Ping Liu, Shanghai (CN); Jingfeng Bai, Shanghai (CN)

(72) Inventors: Xuemin Xu, Shanghai (CN); Aili Zhang, Shanghai (CN); Jianqi Sun, Shanghai (CN); Ping Liu, Shanghai (CN); Wentao Li, Shanghai (CN)

(73) Assignee: MAGI COMPANY LTD., Shanghai (CN)

( * ) Notice: Subject to any disclaimer, the term of this patent is extended or adjusted under 35 U.S.C. 154(b) by 862 days.

(21) Appl. No.: 16/969,817

(22) PCT Filed: Jan. 29, 2019

(86) PCT No.: PCT/CN2019/073727
§ 371 (c)(1),
(2) Date: Aug. 13, 2020

(87) PCT Pub. No.: WO2019/157951
PCT Pub. Date: Aug. 22, 2019

(65) Prior Publication Data
US 2020/0367971 A1    Nov. 26, 2020

(30) Foreign Application Priority Data
Feb. 14, 2018    (CN) .......................... 201810151749.4

(51) Int. Cl.
*A61B 34/10*    (2016.01)
*A61B 18/00*    (2006.01)
(Continued)

(52) U.S. Cl.
CPC .............. *A61B 34/10* (2016.02); *A61B 18/02* (2013.01); *A61B 2018/00041* (2013.01);
(Continued)

(58) Field of Classification Search
CPC .............. A61B 34/10; A61B 2034/101; A61B 2034/104; A61B 2034/107; A61B 18/02
See application file for complete search history.

(56) References Cited

U.S. PATENT DOCUMENTS

2012/0010479 A1    1/2012    Eusemann et al.

FOREIGN PATENT DOCUMENTS

| CN | 102264315 A | 11/2011 |
|----|-------------|---------|
| CN | 105877910 A | 8/2016 |

(Continued)

OTHER PUBLICATIONS

Int'l Search Report dated Apr. 28, 2019 in Int'l Application No. PCT/CN2019/073727.

*Primary Examiner* — Ronald Hupczey, Jr.
(74) *Attorney, Agent, or Firm* — Panitch Schwarze Belisario & Nadel LLP

(57) ABSTRACT

The present application relates to computer-based preoperative planning technology, and discloses a preoperative planning method for multimodal ablation treatment and apparatus thereof, which can automatically provide objective, scientific, and quantitative multimodal ablation planning information. In this method, acquiring parameters of an volume to be ablated; calculating property changes of the tissue caused by performing freezing on the volume according to the parameters of the volume to be ablated, and acquiring a first planning data required for the property changes of the tissue to satisfy a first predetermined condition; further calculating property changes of the tissue caused by performing heating on the volume to acquire a
(Continued)

second planning data required for the property changes of the tissue to satisfy a second predetermined condition based on the properties satisfying the first predetermined condition; outputting the first planning data and the second planning data.

16 Claims, 8 Drawing Sheets

(51) Int. Cl.
*A61B 18/02* (2006.01)
*A61B 18/14* (2006.01)

(52) U.S. Cl.
CPC .............. *A61B 2018/00404* (2013.01); *A61B 2018/00577* (2013.01); *A61B 2018/00791* (2013.01); *A61B 2018/00863* (2013.01); *A61B 2018/00988* (2013.01); *A61B 2018/0293* (2013.01); *A61B 18/1477* (2013.01); *A61B 2034/104* (2016.02); *A61B 2034/105* (2016.02); *A61B 2034/107* (2016.02)

(56) References Cited

FOREIGN PATENT DOCUMENTS

| CN | 106132330 A | 11/2016 | |
|---|---|---|---|
| WO | WO-2010075305 A1 * | 7/2010 | ............. A61B 18/02 |

* cited by examiner

PREOPERATIVE PLANNING METHOD FOR MULTIMODAL ABLATION TREATMENT AND APPARATUS THEREOF

CROSS-REFERENCE TO RELATED APPLICATIONS

This application is a Section 371 of International Application No. PCT/CN2019/073727, filed Jan. 29, 2019, which was published in the Chinese language on Aug. 22, 2019 under International Publication No. WO 2019/157951 A1, which claims priority under 35 U.S.C. § 119 to Chinese Patent Application No. 201810151749.4, filed on Feb. 14, 2018 the disclosures of all of which are incorporated herein by reference.

TECHNICAL FIELD

The present application relates to computer-based planning technology for local thermal ablation, in particular to preoperative planning technology for multimodal ablation treatment, namely liquid nitrogen freezing followed by radio frequency heating through a needle probe.

BACKGROUND OF THE INVENTION

With continuous development of science and technology and medical equipment, new treatment technologies are constantly emerging, especially local ablation based modern tumor minimally invasive treatment which mainly uses ultrasound, CT, MRI and other images to guide percutaneous puncture of the tumor and uses high or low temperature probe causing coagulative necrosis of the tumor, thereby achieving the goal of local ablation of the tumor.

However, there are still many bottleneck problems in the minimally invasive tumor ablation surgery that need to be breakthrough. For example, doctors usually rely on imaging methods such as enhanced CT, MRI, or two-dimensional ultrasound contrast and combine with their own experience to consider needles insertion and treatment options, which lacks of objective and accurate calculation of intraoperative thermal dose and evaluation of uneven heat transfer caused by tumor tissue heterogeneity, and often fails to achieve the desired results.

BRIEF SUMMARY OF THE INVENTION

The purpose of the present application is to provide a preoperative planning method for multimodal ablation treatment, namely liquid nitrogen freezing followed by radio frequency heating through a needle probe, and apparatus thereof, which can automatically provide objective, scientific, and quantitative local multimodal ablation planning information.

In order to solve the above problems, the present application discloses a preoperative planning method for multimodal ablation treatment, comprising:
  acquiring parameters of a target tissue volume to be ablated;
  calculating freezing dosage for acquired property changes of the tissue caused by performing pre-freezing according to both freezing induced mechanical and thermal effect on the biological tissue and the parameters of the volume to be ablated, and acquiring a first planning data required for the property changes of the tissue to satisfy a first predetermined condition;
  further calculating the heating dosage for acquired property changes of the tissue caused by performing heating on the volume to acquire a second planning data required for the property changes of the tissue to satisfy a second predetermined condition based on the properties satisfying the first predetermined condition; and
  outputting the first planning data and the second planning data.

In a preferred embodiment, the outputting of the first planning data and the second planning data, comprises:
  displaying needle insertion scheme for the multimodal ablation and/or resulting temperature field distribution in form of text and/or graphics according to the first planning data and the second planning data.

In a preferred embodiment, the first predetermined condition is that the properties of the tissue reach a state capable of uniformly conducting heat in various directions.

In a preferred embodiment, the properties of the tissue reach a state capable of uniformly conducting heat in all directions, comprises, forming an ice ball in the volume to be ablated, and the ice ball covers the entire volume to be ablated.

In a preferred embodiment, the property changes comprise one or any combination of the following change: change in electrical conductivity, change in thermal conductivity, change in electrolyte distribution, change in blood flow distribution.

In a preferred embodiment, the second predetermined condition comprises in-situ disruption of cells and/or microvessels within the boundary of the volume to be ablated.

In a preferred embodiment, the first planning data comprises one or any combination of the following:
  patient posture, skin puncture point, number of treatment needles, position of treatment needles, insertion path of treatment needles, number and distance of treatment needles withdrawal, freezing power and time, freezing rate.

In a preferred embodiment, the second planning data comprises one or any combination of the following:
  patient posture, skin puncture point, number of treatment needles, position of treatment needles, insertion path of treatment needles, number and distance of treatment needles withdrawal, heating power and time, heating rate.

In a preferred embodiment, the volume to be ablated comprises a tumor.

In a preferred embodiment, the parameters of the volume to be ablated comprise one or any combination of the following:
  the size, shape, relative position and tissue property information of the tumor and other tissues and organs in the volume to be ablated, the blood vessel distribution and the blood perfusion situation of the surrounding tissues.

In a preferred embodiment, the acquiring parameters of the volume to be ablated, comprises,
  performing reconstruction and segmentation according to the patient's preoperative 2D or 3D images, and extracting the size, shape, relative position and tissue property information of the tumor and other tissues and organs; acquiring the blood vessel distribution and the blood perfusion of the tumor and surrounding tissues by imaging methods.

In a preferred embodiment, the "calculating property changes of the tissue caused by performing freezing on the volume according to the parameters of the volume to be ablated, and acquiring a first planning data required for the property changes of the tissue to satisfy a first predetermined condition" further comprises:

considering the influence of tissues and large blood vessels, taking into account blood flow, calculating the number of inserted freezing needles required for tissue pretreatment and the synergy among multiple needles to ensure that the ice ball covers the entire tumor; calculating freezing rate of forming the ice ball and setting the freezing power.

In a preferred embodiment, the calculating of the property changes of the tissue caused by performing freezing on the volume according to the parameters of the volume to be ablated, comprises, acquiring the property changes of the tissue in the volume after frozen by calculating freezing range and temperature field.

In a preferred embodiment, the "further calculating property changes of the tissue caused by performing heating on the volume to acquire a second planning data required for the property changes of the tissue to satisfy a second predetermined condition based on the properties satisfying the first predetermined condition", comprises:

based on coupling of electromagnetic field and temperature field, taking into account the property changes of the tumor tissue after frozen and the synergy among treatment needles, calculating the force required for in-situ disruption of all cells and/or microvessels within the tumor boundary, calculating corresponding heating rate and total thermal dose, revising needle insertion scheme, including the number and position distribution of the treatment needles, to ensure that multimodal ablation treatment can control heating range and its overlap with freezing range to satisfy predetermined requirements.

In a preferred embodiment, after the step of outputting the first planning data and the second planning data, further comprising:

acquiring medical images of pre-inserted treatment needles;

calculating the number and position of actually inserted treatment needles according to the medical images of the pre-inserted treatment needles;

determining whether the number and position of the actually inserted treatment needles are consistent with the first planning data and the second planning data;

if inconsistent, according to the number and position of the actually inserted treatment needles, simulating the temperature field distribution of the tumor cells and action of mechanical force, calculating ablation volume formed by the pre-inserted needles, and revising planning parameters according to the calculated ablation volume, including increasing or decreasing the number of treatment needles, adjusting position distribution of the treatment needles, increasing or decreasing the heating power and time.

In a preferred embodiment, after revising the planning parameters according to the calculated ablation volume, further comprising:

if according to the revised planning parameters, the thermal dose required for in-situ disruption of all tumor cells and/or microvessels within the tumor boundary still not satisfy, then re-planning multimodal ablation plan and revising ablation strategy to ensure complete local ablation of the tumor.

The application also discloses a preoperative planning apparatus for multimodal ablation treatment, comprising an acquiring module, configured to acquire parameters of a volume to be ablated;

a first planning module, configured to calculate property changes of the tissue caused by performing freezing on the volume according to the parameters of the volume to be ablated, and acquire a first planning data required for the property changes of the tissue to satisfy a first predetermined condition;

a second planning module, configured to further calculate the property changes of the tissue caused by performing heating on the volume to acquire a second planning data required for the property changes of the tissue to satisfy a second predetermined condition based on the properties satisfying the first predetermined condition;

an outputting module, output the first planning data and the second planning data.

In a preferred embodiment, the first predetermined condition is that forming an ice ball in the volume to be ablated, and the ice ball covers the entire volume to be ablated;

the second predetermined condition comprises in-situ disruption of cells and/or microvessels within the boundary of the volume to be ablated;

the property changes comprise one or any combination of the following change: change in electrical conductivity, change in thermal conductivity, change in electrolyte distribution, change in blood flow distribution.

In a preferred embodiment, the first planning data comprises one or any combination of the following: patient posture, skin puncture point, number of treatment needles, position of treatment needles, insertion path of treatment needles, number and distance of treatment needles withdrawal, freezing power and time, freezing rate;

patient posture, skin puncture point, number of treatment needles, position of treatment needles, insertion path of treatment needles, number and distance of treatment needles withdrawal, heating power and time, heating rate.

In a preferred embodiment, the volume to be ablated comprises a tumor.

In a preferred embodiment, the acquiring module performs reconstruction and segmentation according to the patient's preoperative 2D or 3D images, and extracts the size, shape, relative position and tissue property information of the tumor and other tissues and organs; acquires the blood vessel distribution and blood perfusion of the tumor and surrounding tissues by imaging methods.

In a preferred embodiment, the first planning module considers the influence of tissues and large blood vessels, takes into account the blood flow, calculates the number of inserted freezing needles required for tissue pretreatment and the synergy among multiple needles to ensure that the ice ball covers the entire tumor; calculates the freezing rate of forming ice balls and sets the freezing power.

In a preferred embodiment, the calculate the property changes of the tissue caused by performing freezing on the volume according to the parameters of the volume to be ablated, comprising, acquiring the property changes of tissue in the volume after frozen by calculating the freezing range and temperature field.

In a preferred embodiment, the second planning module based on coupling of the electromagnetic field and temperature field, takes into account the property changes of the tumor tissue after frozen and the synergy among the treatment needles, calculates the force required in-situ disruption of all cells and/or microvessels within the tumor boundary, calculates corresponding heating rate and total thermal dose, revises needle insertion scheme, comprising the number and position distribution of the treatment needles, to ensure that multimodal ablation treatment can control heating range and its overlap with freezing range to satisfy predetermined requirements.

In a preferred embodiment, further comprising a plan revising module, configured to
- acquire medical images of pre-inserted treatment needles;
- calculate the number and position of actually inserted treatment needles according to the medical images of the pre-inserted treatment needles;
- determine whether the number and position of the actually inserted treatment needles are consistent with the first planning data and the second planning data;
- if inconsistent, according to the number and position of the actually inserted treatment needles, simulate the temperature field distribution of the tumor cells and the action of mechanical force, calculate ablation volume formed by the pre-inserted needles, and revise planning parameters according to the calculated ablation volume, including increasing or decreasing the number of treatment needles, adjusting position distribution of the treatment needles, increasing or decreasing the heating power and time;
- if according to the revised planning parameters, the thermal dose required for in-situ disruption of all tumor cells and/or microvessels within the tumor boundary still not satisfy, then re-plan multimodal ablation plan and revise ablation strategy to ensure complete local ablation of the tumor.

The application also discloses a preoperative planning apparatus for multimodal ablation treatment, comprising:
- a memory for storing computer executable instructions; and
- a processor, configured to implement the steps of the above-described preoperative planning method for multimodal ablation treatment when executing the computer executable instructions.

The present application also discloses a computer readable storage medium that stores computer executable instructions which are executed by a processor to implement the steps of the above-described preoperative planning method for multimodal ablation treatment.

In another preferred embodiment, the above methods and/or apparatus are not used in the treatment and diagnosis of diseases.

Compared with the prior art, the embodiments of the present application can objectively and accurately calculate and evaluate intraoperative thermal dose, its effect range and effects, and can establish an objective, scientific and quantitative preoperative planning for local ablation treatment of the tumor. It is conducive to improving the safety and effectiveness of local ablation therapy for the tumor, and is of great significance for achieving precise treatment.

A large number of technical features are described in the specification of the present application, and are distributed in various technical solutions. If a combination (i.e., a technical solution) of all possible technical features of the present application is listed, the description may be made too long. In order to avoid this problem, the various technical features disclosed in the above summary of the present application, the technical features disclosed in the various embodiments and examples below, and the various technical features disclosed in the drawings can be freely combined with each other to constitute various new technical solutions (all of which are considered to have been described in this specification), unless a combination of such technical features is not technically feasible. For example, feature A+B+C is disclosed in one example, and feature A+B+D+E is disclosed in another example, while features C and D are equivalent technical means that perform the same function, and technically only choose one, not to adopt at the same time. Feature E can be combined with feature C technically. Then, the A+B+C+D scheme should not be regarded as already recorded because of the technical infeasibility, and A+B+C+E scheme should be considered as already documented.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown.

In the drawings.

DETAILED DESCRIPTION OF THE INVENTION

Figure 1:
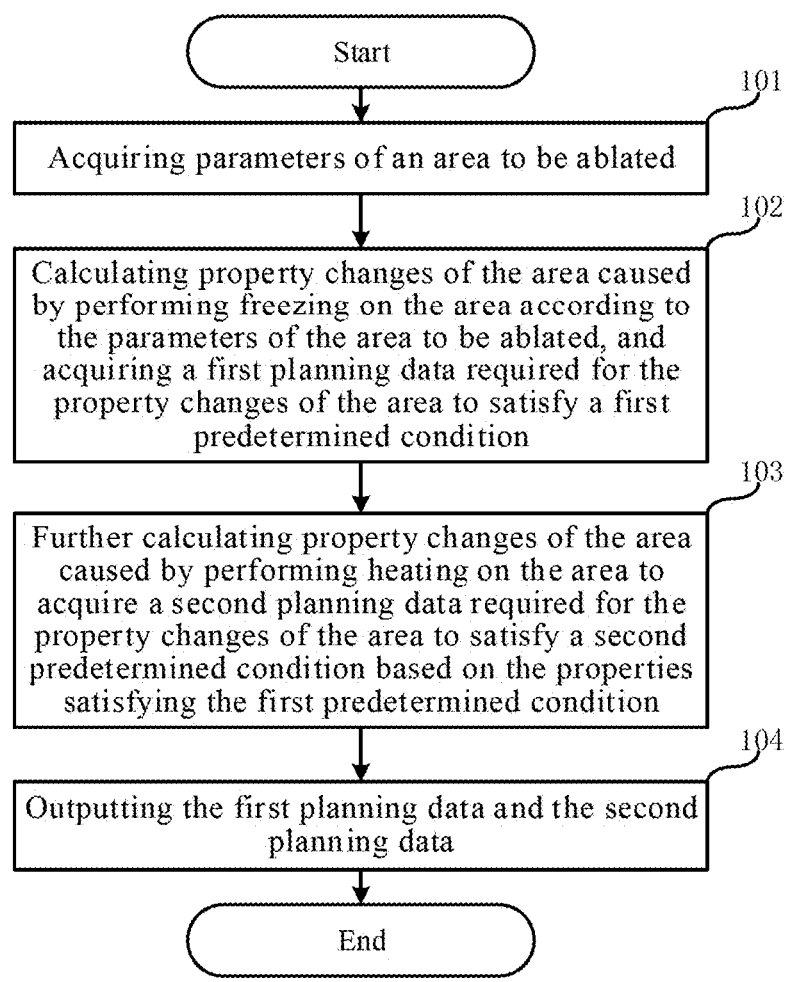
FIG. 1 is a schematic flow chart of a preoperative planning method for multimodal ablation treatment in a first embodiment of the present application.

In the following description, numerous technical details are set forth in order to provide the reader with a better understanding of the present application. However, those skilled in the art can understand that the technical solutions claimed in the present application can be implemented without these technical details and various changes and modifications based on the following embodiments.

It should be noted that the technical solution of the present application does not belong to the treatment and diagnosis method for diseases. The technical solution of this application is only to provide planning information for multimodal ablation therapy. The information is only for the doctor's reference before operation. It does not replace the doctor to directly operate the patient and does not directly affect the human body, so it is not a disease treatment method. In a preferred embodiment, the entire technical solution is executed in a computer system which obtains medical imaging data from an external device (such as a medical imaging device or a storage device for medical imaging)

through a data interface, and gets relevant parameters of the volume to be ablated by analyzing the data, and then combines them with the information obtained from the input device (such as the interactive information input by the doctor through a mouse and a keyboard) to establish a physical model for calculation, and finally outputs planning data on a display in form of graphics or text, and displays the expected effect diagram executed according to the planning data. It can be seen that the essence of this embodiment is a specific computer system for processing medical data and simulating specific physical processes. The technical solution of the present application also does not involve a disease diagnosis method, because before the application of the technical solution, the patient has been definitely diagnosed (typically a tumor-like disease), and the technical solution of the present application does not provide further diagnosis.

Explanation of Some Concepts:

Property: refers to physical property, in the application mainly refers to the physical properties of biological tissues, including electrical conductivity, thermal conductivity, blood flow changes, electrolyte distribution, and so on.

Treatment needle: a needle inserted into the volume to be ablated for freezing and heating. Also called ablation needle. In this application, it is sometimes referred to simply as "needle".

CT: Computed Tomography.

MRI: Magnetic Resonance Imaging, also known as Nuclear Magnetic Resonance Imaging (NMRI).

DWI: Magnetic Resonance Diffusion Weighted Imaging.

Multimode tumor thermal therapy is a novel tumor treatment during which a probe is inserted into the tumor center, and the tumor tissue is pretreated by LN2 freezing before radiofrequency heating. It not only greatly improves the local thermal ablation efficiency, disrupts tumor cells and tumor microcirculation in situ, but also releases active tumor antigens, thereby stimulating specific anti-tumor immune responses and inhibiting tumor recurrence and metastasis. The treatment is applicable to various solid tumors. Based on multiple animal high metastasis tumor models and a large number of experimental results, the effects have been proven, and the survival rate is much higher than surgical resection. Clinical studies have also demonstrated that it can prolong disease-free survival in patients. Unlike other thermal treatments, which uses high or low temperature probe causing coagulative necrosis of the tumor, the effective multimode tumor thermal therapy requires precise control of the tumor boundary temperature to form a transition zone of active tumor antigen exposure, which can be recognized by self-defense immune cells. To ensure a successful immune treatment using the multimode thermal therapy, a special treatment planning protocol is needed.

The following is a summary of some of the innovations of this application:

Taking medical image of the tumor region by the medical imaging device, and the medical image is analyzed and combined with the data input by other input devices, so the parameters of the volume to be ablated (for example, the size, shape, relative position and physical properties of tumors and other tissues in the volume to be ablated, as well as the distribution of blood vessels and blood perfusion in the surrounding tissues, and so on) can be obtained. According to these parameters, establishing a physical model for freezing calculation, calculating freezing dosage for necessary property changes (such as thermal conductivity, electrical conductivity and other physical properties) generated when freezing on the volume to be ablated, and then calculating a first planning data required for the property changes of the tissue to satisfy a first predetermined condition, or to make the physical properties of the tissue satisfy a certain level, wherein the basic requirement of the first predetermined condition is that the physical state of the volume reaches a level that can substantially isotropically conduct the heat of heating, for example, a uniform ice ball covering the entire volume can be formed in the volume to be ablated. After the physical properties of the tissue reaching the above-mentioned level, establishing a physical model on this basis to calculate property changes caused by heating on the volume, and then calculating a second planning data required for a second predetermined condition (for example, causing in-situ disruption of the cells and/or microvessels within the boundary of the volume). After that, displaying the planning data on a display device in form of graphics or text, or outputting in other ways (such as, saving to a database). Through the above scheme, the doctor can know ideal plan before ablation operation, including the number, position, needle insertion path, freezing power of each treatment needle, freezing time, heating power, heating time and other key information, and also ablation range based on this plan, which greatly improves the success rate of surgery.

Establishing a physical model for heating calculation on the basis of the properties that satisfy the first predetermined condition can greatly simplify the physical model for heating calculation and speed up the calculation, because the physical model no longer needs to consider different components with very different thermal conductivity properties (for example, the obvious difference in thermal conductivity between tumor tissue and blood).

An important point of this application is that the properties of the tissue to be ablated must be changed to a certain degree (i.e., the first predetermined condition) during pre-freezing, or that the properties of the tissue to be ablated have undergone a qualitative change, this certain degree is the extent to which the physical state of the volume is able to conduct the heat of heating approximately isotropically, for example, a uniform ice ball covering the entire volume can be formed in the volume to be ablated. The heating on this volume is performed after the properties reach the above-mentioned degree. When the freezing is not able to reach the above-mentioned degree, if the ablation volume is heated directly, due to the relatively complex composition of this volume (there are both tumor tissue and normal tissue, as well as various sizes of blood vessels and blood therein), it will cause the problem of uneven heating when the volume is heated, that is, after heating for a certain period of time, some parts have been overheated, while the heating of other parts may be far from enough, which will seriously affect the effect of thermal ablation.

Another important point of this application is that after a uniform ice ball covering the entire volume has been formed in the volume to be ablated, performing heating and the heating power (corresponding to the heating rate) and the heat dose have specific requirements (the second predetermined condition), that is, in-situ disruption of the cells and/or microvessels within the boundary of the volume to be ablated. The disruption of microvessels eliminates the heat diffusion effect of blood flow in tumor tissue, greatly improving the efficiency of heating and ablation; the in-situ disruption of cells can release antigens, which may stimulate the body's immune response and greatly reduce recurrence chance of cancer. In addition, there are upper limits to the power and dose of freezing and heating, or the first or second predetermined conditions may be further limited, that is, the antigen may not be inactivated.

Optionally, after outputting preliminary planning data, the system can further input medical images of pre-inserted treatment needles through an interface with medical imaging equipment, and perform image analysis on these medical images to obtain the actual number and position of inserted treatment needles, based on this information, calculate whether the preliminary planned freezing power, freezing time, heating power, heating time can reach the expected effect (for example, in-situ disruption of the cells and/or microvessels within the boundary of the volume to be ablated), if not, calculate the freezing power, freezing time, heating power, heating time required to achieve the desired effect based on the number and position of the actual inserted treatment needles, and even add the needles or adjust the position of some treatment needles, the new planning information and its effects are displayed to the doctor in form of graphics or text to provide new help information for the doctor.

In order to make the objects, technical solutions and advantages of the present application clearer, embodiments of the present application will be further described in detail below with reference to the accompanying drawings.

The multimodal ablation technique in the embodiment of the present application is a tumor thermal ablation minimally invasive treatment surgery in which change the properties of the tissue and the blood flow state by pre-freezing the tumor tissue, which improves the heating efficiency, effectively achieves in-situ disruption of tumor cells and/or tumor tissue microvessels, releases tumor antigen to its greatest extent, and stimulates the body's anti-tumor immune response.

Existing preoperative planning technologies for ablation are preoperative planning for single radiofrequency ablation or single cryoablation to treat tumor, but this technology can be used for preoperative planning for single radiofrequency heating ablation, single cryoablation, and also multimodal ablation surgery; the existing technologies do not accurately analyze the thermal dose during preoperative planning, and generally simplify the volume to be ablated to an ellipsoid, do not consider the synergy among multiple ablation needles, nor do they consider the effect on the thermal dose in the volume to be ablated when there are large blood vessels near the tumor, the accuracy of the planning scheme is not high enough. The innovation of this technology lies in the addition of existing technologies: ① based on the principle of biological heat and mass transfer and thermal energy induced biological effect, accurately calculate the thermal dose generated after the property changes of tissue (including electrical conductivity and thermal conductivity) and at a set power to ensure that multimodal ablation treatment can disrupt tumor cells and the tumor tissue microvessels system to the greatest extent, greatly improving ablation efficiency, and maximizing release of tumor antigens, stimulating the body's immune response. ② during multimodal ablation treatment, heating range and its overlap with freezing range can be controlled, thereby maximizing the stimulation of the body's immune response. ③ can quickly calculate the interaction between single-needle ablation or multi-needle ablation, corresponding temperature field distribution and ablation volume. ④ in the preoperative planning, the influence of the thermal dose on the volume to be ablated under the influence of blood vessels near the tumor can be considered. ⑤ based on the above conditions, automatically plan the best multimodal ablation treatment plan.

The first embodiment of the present invention relates to a preoperative planning method for multimodal ablation treatment. FIG. 1 is a schematic flowchart of the preoperative planning method for multimodal ablation treatment. The preoperative planning method for multimodal ablation treatment comprising:

In step 101, acquiring parameters of an volume to be ablated. Preferably, the volume to be ablated comprises a tumor. Of course, the volume to be ablated may also be other designated local tissues, all or part of an organ, and so on. The parameters of the volume to be ablated may comprise: the size, shape, relative position and physical property information of the tumor and other tissues and organs in the volume to be ablated, the blood vessel distribution and blood perfusion of the surrounding tissue, and so on.

Then, into step 102, calculating property changes of the tissue caused by performing freezing on the volume according to the parameters of the volume to be ablated, and acquiring a first planning data required for the property changes of the tissue to satisfy a first predetermined condition. Preferably, the first predetermined condition is that the physical properties of the tissue to be ablated reach a state capable of uniformly conducting heat in various directions. Preferably, the first predetermined condition is that the volume to be ablated forms an ice ball, and the ice ball covers the entire volume to be ablated.

After that, into step 103, further calculating property changes of the tissue caused by performing heating on the volume to acquire a second planning data required for the property changes of the tissue to satisfy a second predetermined condition based on the properties satisfying the first predetermined condition. Preferably, the second predetermined condition comprises in-situ disruption of cells and/or microvessels within the boundary of the volume to be ablated. Optionally, the second predetermined condition comprises in-situ disruption of the cells and/or microvessels within the boundary of the volume to be ablated and remaining active of the antigens in the cells. Optionally, making certain adjustments to the first planning data when calculating the second planning data.

Thereafter, into step 104, outputting the first planning data and the second planning data. The final output planning result information may be obtained based on the first and second planning data, and may not necessarily comprise all the content in the first and second planning data according to different application scenarios. Optionally, displaying the multimodal ablation needle insertion scheme and/or the formed temperature field range in form of text and/or graphics on a display. The needle insertion scheme comprises some or all of the information in the first and second planning data. Optionally, sending the first and second planning data through a communication network, for example, through e-mail or instant messaging tools. Optionally, outputting the first and second planning data to a database.

The technical solution can objectively and accurately calculate and evaluate the intraoperative thermal dose, its effect range and effects, and can establish an objective, scientific and quantitative preoperative planning for local ablation treatment of tumors, which is conducive to improving the safety and effectiveness of local ablation therapy for tumors, and is of great significance for achieving precise treatment.

The details of this embodiment are described in detail below:

The property changes may comprise one or any combination of the following change: change in electrical conductivity, change in thermal conductivity, change in electrolyte distribution, change in blood flow distribution, and so on.

The first planning data may comprise one or any combination of the following:
  patient posture, skin puncture point, number of treatment needles, position of treatment needles, insertion path of treatment needles, number and distance of treatment needles withdrawal, freezing power and time, freezing rate, and so on.

The second planning data may comprise one or any combination of the following:
  patient posture, skin puncture point, number of treatment needles, position of treatment needles, insertion path of treatment needles, number and distance of treatment needles withdrawal, heating power and time, heating rate, and so on.

Preferably, in the first planning data and the second planning data, the number of treatment needles and the position of each treatment needle are the same. In this way, the heating can be performed without adjusting the treatment needle after the freezing is completed.

The implementation method of step 101 may be various. Preferably, performing reconstruction and segmentation according to the patient's preoperative 2D or 3D images, and extracting the size, shape, relative position and tissue property information of the tumor and other tissues and organs; acquiring the blood vessel distribution and the blood perfusion of the tumor and surrounding tissues by imaging methods. Optionally, the computer interacts with the doctor through the interactive interface, and the doctor inputs the parameters of the volume to be ablated to the computer through input devices such as a keyboard and a mouse. Optionally, the computer connects to the medical imaging equipment (such as X-ray machine, CT, MRI, and so on) through a communication interface, and receives medical images of the patient from the interface, and obtains part of the parameters of the volume to be ablated by analyzing these medical images. Optionally, the computer connects to a database server to obtain at least a part of the parameters of the volume to be ablated from the database.

Preferably, when implementing step 102, calculating property changes of the tissue caused by freezing the volume according to the parameters of the volume to be ablated, and acquiring a first planning data required for the property changes of the tissue to satisfy a first predetermined condition.

Preferably, "calculating of the property changes of the tissue caused by performing freezing on the volume according to the parameters of the volume to be ablated" in step 102 comprises, acquiring the property changes of the tissue in the volume after frozen by calculating freezing range and temperature field.

Preferably, step 103 further comprises: based on coupling of electromagnetic field and temperature field, taking into account the property changes of the tumor tissue after frozen and the synergy among treatment needles, calculating the force required for in-situ disruption of all cells and/or microvessels within the tumor boundary, calculating corresponding heating rate and total thermal dose, revising needle insertion scheme, including the number and position distribution of the treatment needles, to ensure that multimodal ablation treatment can control heating range and its overlap with freezing range to satisfy predetermined requirements.

Preferably, after step 104, the planning data may also be revised according to the actual pre-inserted needles situation. Specifically, the following steps may be enclosed:
  acquiring medical images of pre-inserted treatment needles;
  calculating the number and position of actually inserted treatment needles according to the medical images of the pre-inserted treatment needles;
  determining whether the number and position of the actually inserted treatment needles are consistent with the first planning data and the second planning data;
  if inconsistent, according to the number and position of the actually inserted treatment needles, simulating the temperature field distribution of the tumor cells and action of mechanical force, calculating ablation volume formed by the pre-inserted needles, and revising planning parameters according to the calculated ablation volume, including increasing or decreasing the number of treatment needles, adjusting position distribution of the treatment needles, increasing or decreasing the heating power and time;
  if according to the revised planning parameters, the thermal dose required for in-situ disruption of all tumor cells and/or microvessels within the tumor boundary still not satisfy, then re-planning multimodal ablation plan and revising ablation strategy to ensure complete local ablation of the tumor.

Figure 2:
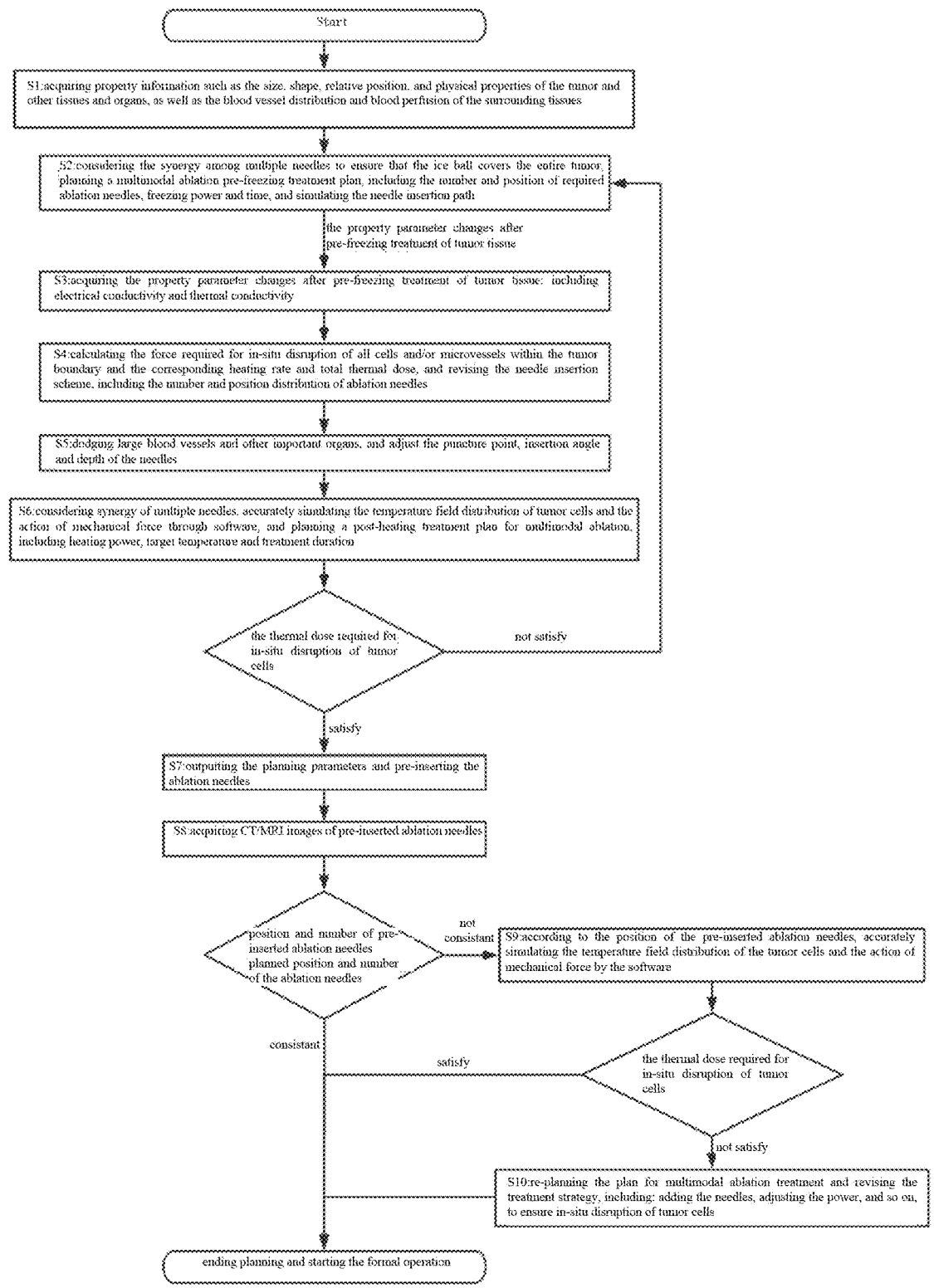
FIG. 2 is a schematic flowchart of an embodiment in a first implementation manner of the present application.

To better understand the above method implementation, a specific example is given below. The flowchart of this embodiment is shown in FIG. 2.

Step S1: acquiring property information such as the size, shape, relative position, and physical properties of the tumor and other tissues and organs, as well as the blood vessel distribution and blood perfusion of the surrounding tissues.

This step can be implemented in various conventional methods. The blood vessels here comprise not only the small blood vessels distributed near the tumor, but also the large blood vessels distributed near the tumor.

Step S2: considering the synergy among multiple needles to ensure that the ice ball covers the entire tumor, planning a multimodal ablation pre-freezing treatment plan, including the number and position of required ablation needles, freezing power and time, and simulating the needle insertion path. The pre-freezing in this embodiment refers to the same process as freezing above.

Specifically, this step comprises the following process:
  ① planning pre-freezing plan for multimodal ablation treatment
  this process is to quickly calculate the number and position of ablation needles, freezing power and time required to cover the entire tumor with the ice ball by the software under the synergy among multiple needles.
  ② simulating the needle insertion path
  through real-time interaction with the doctor, this process can set needle skin puncture point, simulate the needle insertion path, and use the software to display the simulated ablation range after inserting needles.

Step S3: acquiring the property parameter changes after pre-freezing treatment of tumor tissue: including electrical conductivity and thermal conductivity Specifically, when the tumor tissue is pre-frozen, its property parameters will change.

Acquiring the changed property parameters through calculation, and bring them into the next planning step S4.

Step S4: calculating the force required for in-situ disruption of all cells and/or microvessels within the tumor boundary and the corresponding heating rate and total thermal dose, and revising the needle insertion scheme, including the number and position distribution of ablation needles.

Specifically, this step comprises the following process:
① calculating the force required for in-situ disruption of all cells and/or microvessels within the tumor boundary and the corresponding heating rate and total thermal dose;
the calculation is to quickly calculate the force required for in-situ disruption of all cells within the tumor boundary and the corresponding heating rate and total thermal dose after pre-frozen.
② revising needle insertion scheme.
this process is based on the above-mentioned data to revise the needle insertion scheme, including the number and position distribution of ablation needles, and then to achieve in-situ disruption of all cells and/or microvessels within the tumor boundary.

Step S5: dodging large blood vessels and other important organs, and adjust the puncture point, insertion angle and depth of the needles.

Here can interact with the doctor to adjust the puncture point, insertion angle and depth of the needles, or automatically revise by the software.

Step S6: considering synergy among multiple needles, accurately simulating the temperature field distribution of tumor cells and the action of mechanical force through software, and planning a post-heating treatment plan for multimodal ablation, including heating power, target temperature and treatment duration.

Specifically, this step comprises the following process:
① planning post-heating plan for multimodal ablation treatment
the process is to quickly calculate the temperature field distribution of the tumor tissue and the action of mechanical force, as well as the required heating power, target temperature and treatment time through the software under the consideration of synergy among multiple needles.
② determining whether it is satisfied the thermal dose required for in-situ disruption of tumor cells and microvessels.
quickly calculating and analyzing through the software, if the planned solution satisfies the thermal dose required for in-situ disruption of tumor cells and microvessels, step S7 is performed; if not, steps S2 to S6 are repeated until in-situ disruption of the tumor cells.

Step S7: outputting the planning parameters and pre-inserting the ablation needles.
that is, the doctor performs pre-inserting ablation needles on the patient according to the planning parameters.

Step S8: acquiring CT/MRI images of pre-inserted ablation needles.
Specifically, this step comprises the following process:
acquiring CT/MRI images of pre-inserted ablation needles, and using image processing to determine whether the position and number of pre-inserted ablation needles are consistent with the planned position and number of the ablation needles. If they are consistent, ending planning and starting the formal operation; if not, executing steps S9-S10 until in-situ disruption of the tumor cells and/or microvessels.

Step S9: according to the position of the pre-inserted ablation needles, accurately simulating the temperature field distribution of the tumor cells and the action of mechanical force by the software.

Here, under the condition that the position of the pre-inserted ablation needles is unchanged, recalculating the current temperature field distribution of tumor cells and action of mechanical force through the software. At the same time, determining whether the thermal dose required for in-situ disruption of the tumor cells is satisfied, if satisfied, ending planning and starting the formal operation; if not satisfied, executing step S10.

Step S10: re-planning the plan for multimodal ablation treatment and revising the treatment strategy, including: adding the needles, adjusting the power, and so on.

Here is after pre-inserting ablation needles, when temperature field of the tumor cells simulated by the software cannot satisfy in-situ disruption of the tumor cells and microvessels, the treatment strategy is revised by adding the needles, changing the power, and so on, so as to achieving in-situ disruption of the tumor cells and microvessels.

Figure 3:
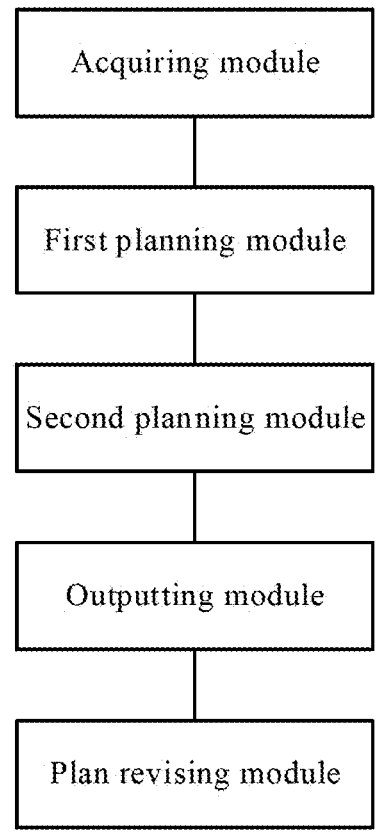
FIG. 3 is a schematic structural diagram of a preoperative planning apparatus for multimodal ablation treatment in a second embodiment of the present application.

The second embodiment of the present invention relates to a preoperative planning apparatus for multimodal ablation treatment. FIG. 3 is a schematic structural diagram of the preoperative planning apparatus for multimodal ablation treatment. The preoperative planning apparatus for multimodal ablation treatment comprises:
an acquiring module, configured to acquire parameters of an volume to be ablated;
a first planning module, configured to calculate property changes of the tissue caused by performing freezing on the volume according to the parameters of the volume to be ablated, and acquire a first planning data required for the property changes of the tissue to satisfy a first predetermined condition;
a second planning module, configured to further calculate property changes of the tissue caused by performing heating on the volume to acquire a second planning data required for the property changes of the tissue to satisfy a second predetermined condition based on the properties satisfying the first predetermined condition;
an outputting module, output the first planning data and the second planning data.

The acquiring module can be implemented in various ways. Optionally, the acquiring module comprises an interface connected to a medical imaging device and an image analysis unit, through which the medical image is obtained, and performs reconstruction and segmentation according to the patient's preoperative 2D or 3D images, and extracts the size, shape, relative position and tissue property information of the tumor and other tissues and organs; acquires the blood vessel distribution and blood perfusion of the tumor and surrounding tissues by imaging methods. The interface may be a network interface, a communication interface, or the like. The image analysis unit may base on traditional medical image analysis technology, and may base on AI (artificial intelligence) technology. Optionally, the acquiring module comprises input devices such as a mouse, a keyboard, and a touch screen, and various parameters of the volume to be ablated are obtained through these input devices.

Preferably, the first predetermined condition is that the volume to be ablated forms an ice ball and the ice ball covers the entire volume to be ablated. The second predetermined condition comprises in-situ disruption of cells and/or microvessels within the boundary of the volume to be ablated.

Preferably, the property changes comprise changes in electrical conductivity and/or in thermal conductivity. Preferably, the property changes comprise change in electrolyte distribution, change in blood flow distribution, and the like.

The first planning data comprises one or any combination of the following:
patient posture, skin puncture point, number of treatment needles, position of treatment needles, insertion path of treatment needles, number and distance of treatment needles withdrawal, freezing power and time, freezing rate, and so on.

The second planning data comprises one or any combination of the following:
patient posture, skin puncture point, number of treatment needles, position of treatment needles, insertion path of treatment needles, number and distance of treatment needles withdrawal, heating power and time, heating rate, and so on.

Preferably, in the first planning data and the second planning data, the number of treatment needles and the position of each treatment needle are the same. In this way, the heating can be performed without adjusting the treatment needles after the freezing is completed.

Preferably, the volume to be ablated comprises a tumor.

Preferably, the first planning module considers the influence of tissues and large blood vessels, takes into account the blood flow, calculates the number of inserted freezing needles required for tissue pretreatment and the synergy among multiple needles to ensure that the ice ball covers the entire tumor; calculates the freezing rate of forming ice balls and sets the freezing power.

Preferably, when the first planning module calculates the property changes of the tissue caused by performing freezing on the volume according to the parameters of the volume to be ablated, acquires the property changes of the tissue in the volume after frozen by calculating freezing range and temperature field.

Preferably, the second planning module based on coupling of the electromagnetic field and temperature field, takes into account the property changes of the tumor tissue after frozen and the synergy among the treatment needles, calculates the force required in-situ disruption of all cells and/or microvessels within the tumor boundary, calculates corresponding heating rate and total thermal dose, revises needle insertion scheme, comprising the number and position distribution of the treatment needles, to ensure that multimodal ablation treatment can control heating range and its overlap with freezing range to satisfy predetermined requirements.

Preferably, the preoperative planning apparatus for multimodal ablation treatment further comprises a plan revising module, configured to
acquire medical images of pre-inserted treatment needles;
calculate the number and position of actually inserted treatment needles according to the medical images of the pre-inserted treatment needles;
determine whether the number and position of the actually inserted treatment needles are consistent with the first planning data and the second planning data;
if inconsistent, according to the number and position of the actually inserted treatment needles, simulate the temperature field distribution of the tumor cells and the action of mechanical force, calculate ablation volume formed by the pre-inserted needles, and revise planning parameters according to the calculated ablation volume, including increasing or decreasing the number of treatment needles, adjusting position distribution of the treatment needles, increasing or decreasing the heating power and time;
if according to the revised planning parameters, the thermal dose required for in-situ disruption of all tumor cells and/or microvessels within the tumor boundary still not satisfy, then re-plan multimodal ablation plan and revise ablation strategy to ensure complete local ablation of the tumor.

The first embodiment is a method embodiment corresponding to this embodiment, and this embodiment can be implemented in cooperation with the first embodiment. The relevant technical details mentioned in the first embodiment are still valid in this embodiment, and in order to reduce repetition, they will not be repeated here. Correspondingly, the relevant technical details mentioned in this embodiment can also be applied in the first embodiment.

Finally, summarizing some of the main points of the present invention as follow:
1) The present invention comprises a preoperative planning method for multimodal ablation treatment and an apparatus thereof, and is firstly to propose the concept of multimodal ablation treatment;
2) In addition to the size, shape, and relative position of the tumor and surrounding tissues and organs, the main collection parameters also comprise tissue physical property information (including electrical conductivity, thermal conductivity, blood flow changes, and electrolyte distribution); and acquiring blood vessel distribution and blood perfusion of surrounding tissues through imaging (such as DWI images);
3) The first step of planning is simulating pre-freezing of the tumor, in order to cause property change of the tissue (including electrical conductivity, thermal conductivity, blood flow change, electrolyte distribution), setting an appropriate freezing rate (freezing power);
4) The key to preoperative planning is calculating the force required for in-situ disruption of the cells and/or microvessels within the tumor boundary, thereby calculating the heating rate and the total thermal dose. In this process, a coupling calculation of electromagnetic and temperature fields is required, At the same time considering the synergy among multiple needles, revising the needle insertion scheme, including the number and position distribution of ablation needles, so as to determining the heating rate (heating power);
5) The indicators (parameters) given by the preoperative planning include ① proper posture; ② determining the skin puncture point and needle insertion path; ③ the number, position, path, number and distance of needles withdrawal; ④ the power required for the pre-freezing process, freezing rate and treatment time; ⑤ thermal ablation power, heating rate and treatment time;
6) The preoperative planning apparatus for multimodal ablation treatment is expressed in a modular manner and protected as a carrier of the method.

Figure 4:
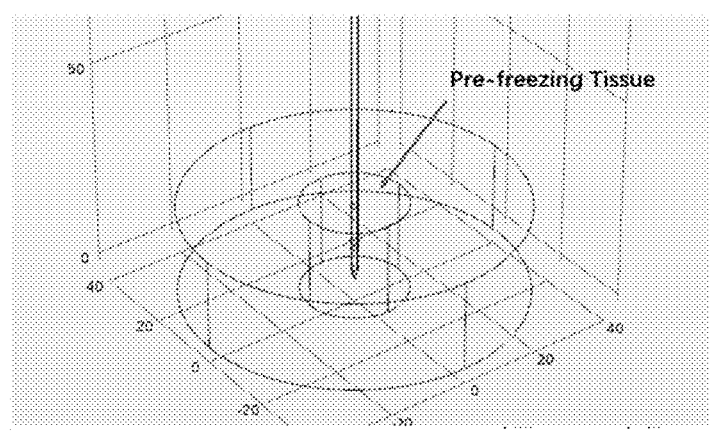
FIG. 4 is a schematic diagram of a calculation model in an embodiment of the present application.

The following describes the physical model used in a specific embodiment of the present application:

In the preoperative planning, the body tissue is simplified to a cylinder as shown in FIG. 4 below. The diameter of the cylinder is 8 cm and the height is 2.25 cm. The pre-freezing treatment volume is simplified to a small cylinder with a diameter of 2.5 cm and a height of 2.25 cm.

Figure 9:
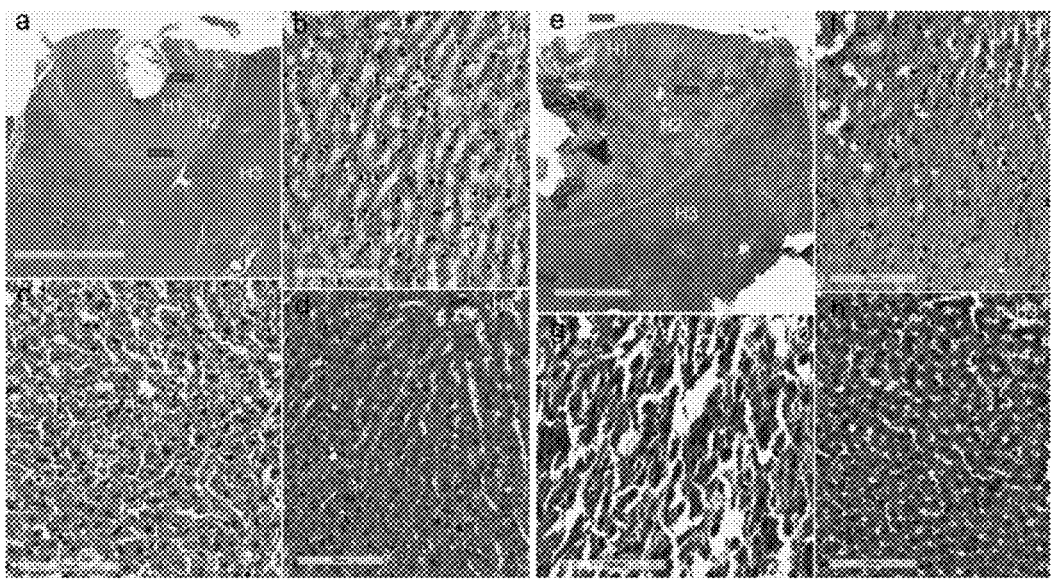
FIG. 9 is a tissue slice diagram in an embodiment of the present application.

For the freezing process, the Pennes biological heat transfer equation is used to describe the heat transfer process in the tissue:

$$\rho c \frac{\partial T}{\partial t} = \nabla \cdot k \nabla T + \omega_b \rho_b c_b \cdot (T - T_b) + q_m \qquad (1)$$

wherein $\rho$ is mass density, c is specific heat capacity, T is tissue temperature, and k is thermal conductivity, $\omega_b$ is blood perfusion rate, and the subscript b represents blood. During heating, its metabolic heat production is negligible: $q_m=0$ Due to phase changes that occurs during the freezing process, the thermophysical properties of the tissue will change as the temperature changes:

(1) the thermal conductivity gradually increases with the solidification of the tissue, above 0° C., the thermal conductivity is 0.51 W/(m·K), between 0° C. and −10° C., the thermal conductivity of the tissue changes linearly, and reaches 1.56 W/(m·K) at −10° C.; the thermal conductivity of the tissue no longer changes after the temperature is lower than −10° C., and remains at 1.56 W/(m·K), as shown in FIG. 9.

Figure 10:
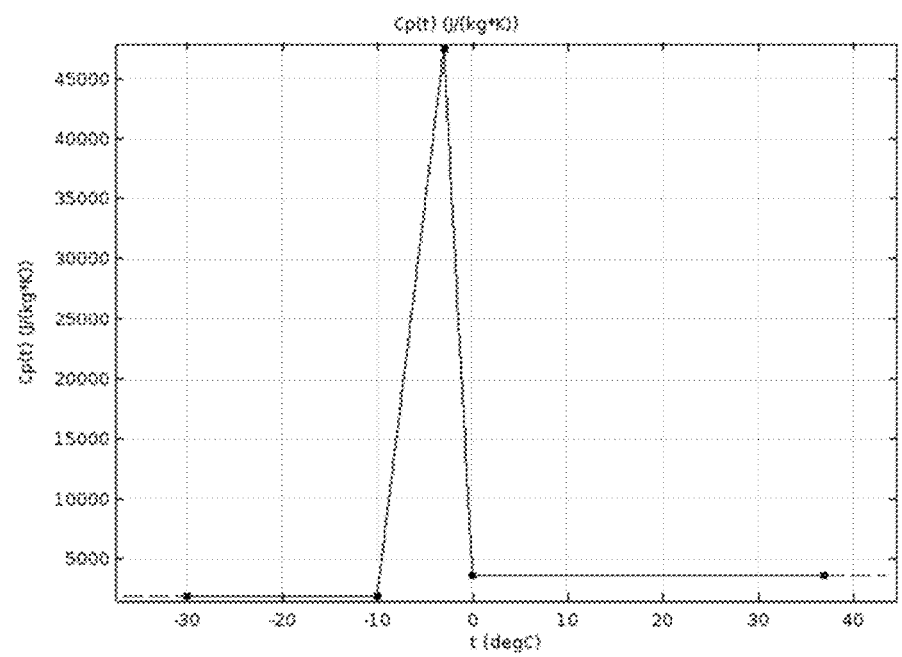
FIGS. 10-13 are related charts of the freezing process in an embodiment of the present application

(2) the specific heat of the tissue is constant when it is higher than 0° C., 3.689 kJ/kg K, and it is also constant when the temperature is lower than −10° C., 1.997 kJ/kg K. However, the tissue will undergo a phase change and produce latent heat of phase change between them. In this application, an effective specific heat value is used to represent the latent heat, the latent heat of the phase change of the tumor is 250 kJ/kg, so according to the calculation, this application will use −3° C. as an effective Peak value of specific heat, effective specific heat value is 47.509 kJ/(kg K), as shown in FIG. 10.

Figure 11:
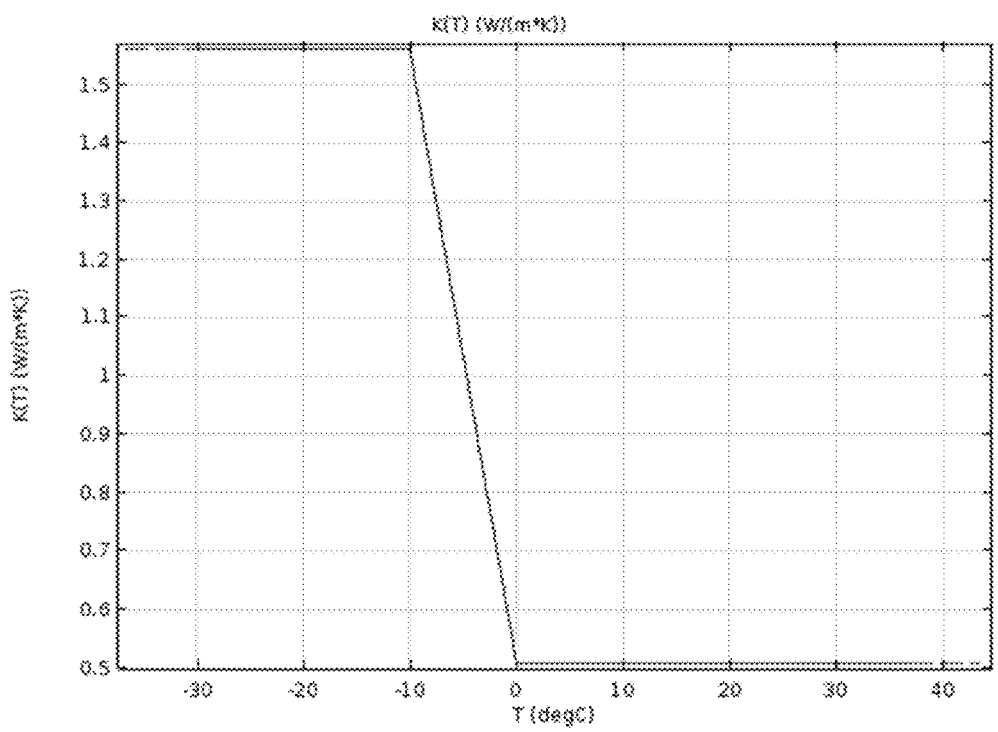

(3) the blood perfusion rate is set to a fixed value of 0.016 (1/s) when the temperature is higher than 0° C., the temperature drops to 0° C. and the blood perfusion system is destroyed, and the blood perfusion rate is always 0, as shown in FIG. 11.

Figure 12:
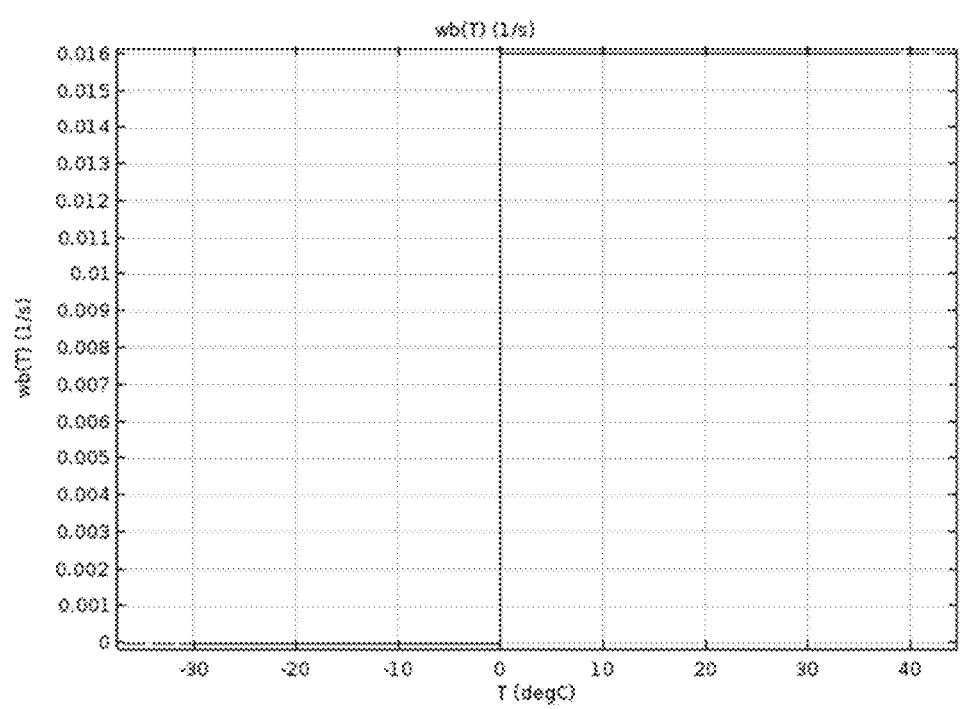
Figure 13:
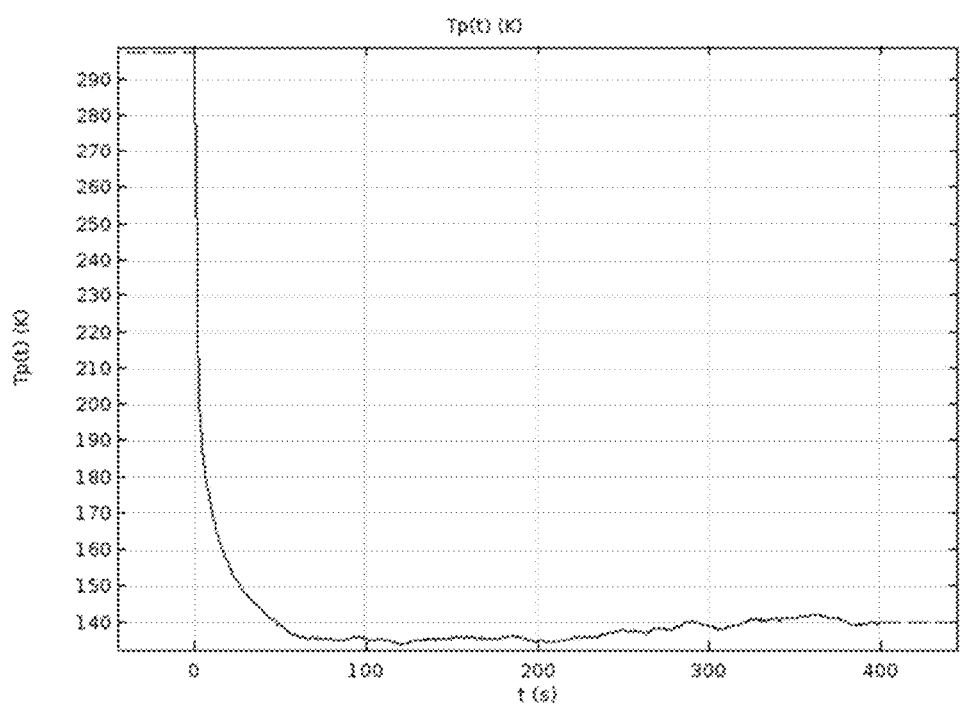

The temperature of the surface of the frozen needles change with time, and their temperature condition is (FIG. 12):

$$T_P=T(t) \quad (2)$$

Using natural convection boundary conditions for the exposed external surface:

$$k\nabla T|_{boundary}=h_s(T_{air}-T) \quad (3)$$

wherein $h_s$ is set to 25 W/m2·K, $T_{air}$ is 25° C. The initial temperature of the tissue and blood is set at 37° C. The subscript boundary represents the boundary, and the subscript air represents the air.

Other properties used in the model are shown in Table 1. Since the RF frequency used is 460 kHz, its wavelength is much larger than the size of the tissue.

Therefore, a quasi-static approximation is used to simulate the electric field:

$$\nabla \cdot [\sigma(T) \cdot \nabla V]=0 \quad (4)$$

wherein V is voltage and σ is conductivity.

The boundary conditions of the electric field are as follows:

$$V_{positive-electrod}=\text{constant } V_{negative-electrod}=0 \quad (5)$$

$$\nabla V=0 \quad (6)$$

Equation (5) describes applying a constant voltage between two electrodes, while equation (6) describes using Neumann boundary conditions at the air-tissue interface of the model.

The heating process is described as follows:

The heat source ($q_h$) generated by the electric field can be calculated by the following formula:

$$q_h=\sigma(\nabla V)^2 \quad (7)$$

The Pennes biological heat transfer equation is used to describe the heat transfer process in the tissue:

$$\rho c \frac{\partial T}{\partial t} = \nabla \cdot k\nabla T + \omega_b \rho_b c_b \cdot (T-T_b) + q_m + q_h \quad (8)$$

Wherein ρ is mass density, c is specific heat capacity, T is the tissue temperature, k is thermal conductivity, and $\omega_b$ is blood perfusion rate. During the heating process, its metabolic heat production is negligible: $q_m=0$ Using natural convection boundary conditions for the exposed external surface:

$$k\nabla T|_{boundary}=h_s(T_{air}-T) \quad (9)$$

wherein $h_s$ is set to 25 W/m²·K, $T_{air}$ is 25° C.

For normal tissues, the initial temperature of the tissue and blood is set at 37.5° C., and for pre-frozen tissue, the initial temperature is set at 36.5° C. The liver properties used in the model are shown in Table 1. The change in electrical conductivity from normal tissue to frozen tissue can be obtained through experiments. The thermal conductivity of normal liver tissue is 0.49 (W/mK) in the literature. For frozen tissues, blood flow stops completely, which may cause change in apparent thermal conductivity of the tissue. Experiments prove that the process of alternating freezing and heating will cause severe vascular injury, so the blood perfusion rate of the tissue after pre-frozen is set to zero. During radiofrequency heating, the blood perfusion rate of normal liver tissue is greatly affected by tissue temperature, so the blood perfusion rate of normal tissue is determined by simulation.

TABLE 1

| Properties used in digital simulation models | | |
|---|---|---|
| Pproperties (unit) | Normal liver tissue | Frozen tissue |
| Blood perfusion rate (1/s) | Measured (T ≤ 50° C.); 0 (T > 50° C.) | 0 |
| Electrical conductivity (S/m) | 0.402 * | 0.38 * |
| Thermal conductivity [W/(m · K)] | 0.49 | Measured |
| Specific heat capacity of liver (J/kg · K) | 3600 | |
| Density of liver (kg/m³) | 1060 | |
| Specific heat capacity of blood (J/kg · K) | 4180 | |
| Density of blood (kg/m³) | 1000 | |

* Conductivity has been measured by measurement experiment

Figure 5:
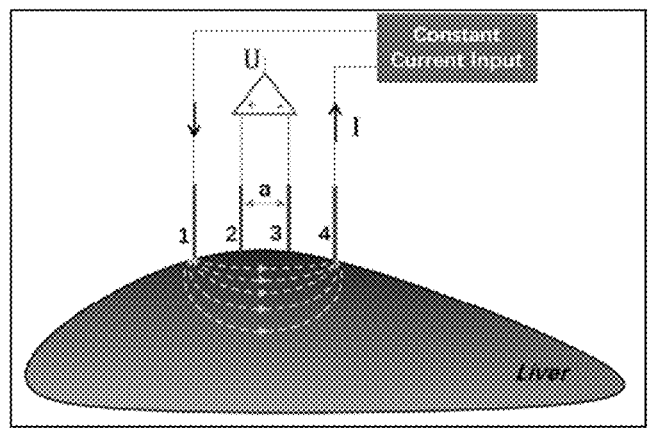
FIG. 5 is a schematic diagram of conductivity measurement in an embodiment of the present application.

The following describes the experiment for measuring conductivity:

The electrical conductivity is calculated using four-electrode method to measure impedance. A constant current is applied to two external electrodes, while two internal electrodes are used to measure the potential difference. Steendijk's research shows that as long as the tissue thickness is 1.95 times of the distance between electrodes, there can use semi-infinite model. The distance between electrodes used here is 5 mm, and the thickness of the rabbit liver is 20 mm, so it is reasonable to use the semi-infinite model. As shown in FIG. 5, the laboratory-made four-electrode probe is in close contact with the tissue surface, and the distance between two adjacent electrodes is 5 mm. Using an impedance analyzer (Agilent, E4980A), between electrodes 1 and 4, apply an alternating current in the range of 1 kHz to 2 MHz (effective value is 20 mA). The electrodes 2 and 3 make a voltage measurement U(ω), Thus obtaining the tissue impedance at different frequencies and describing it with an imaginary number $Z(\omega)=|Z|e^{j\theta}$. The impedance analyzer directly reads $|Z|$ and phase $\theta$.

Three rabbits are used for conductivity measurement in the experiment. First performing a laparotomy to expose their livers. For each rabbit, choosing one leaf liver for the experiment, and dividing the measurement process into three different states: (a) normal (b) pre-freezing (c) heating after pre-frozen. Before heating treatment, the impedance $Z(\omega)$ is recorded as state (a). Then, the tissue is frozen using the same solution as the above experiment. After thawing, the second measurement is performed as state (b). Subsequently, the pre-frozen volume is heated at a voltage of 460 kHz-22.5V for 30 s. Here a lower voltage and a shorter heating time are used to avoid tissue coagulation. After heating, the tissue is cooled to normal temperature. Then, the third measurement is performed as state (c). For each rabbit, the impedance measurement results are obtained in three different states (normal, pre-freezing and heating after pre-frozen) and different frequencies.

Assuming that the tissue is a semi-infinite conductor, the tissue conductivity can be obtained from the following formula:

$$\sigma(\omega) = 1/2\pi a R(\omega) \qquad (10)$$

wherein a is distance between two adjacent electrodes ($\alpha$=5 mm), and $R(\omega)$ is tissue equivalent resistance.

Considering the tissue as a parallel circuit of resistor and capacitor, the equivalent resistance of the tissue can be calculated from its impedance $Z(\omega)$:

$$1/Z(\omega) = 1/R(\omega) + j\omega C(\omega) \qquad (11)$$

$$R(\omega) = 1/Re[Z(\omega)] \qquad (12)$$

Figure 6:
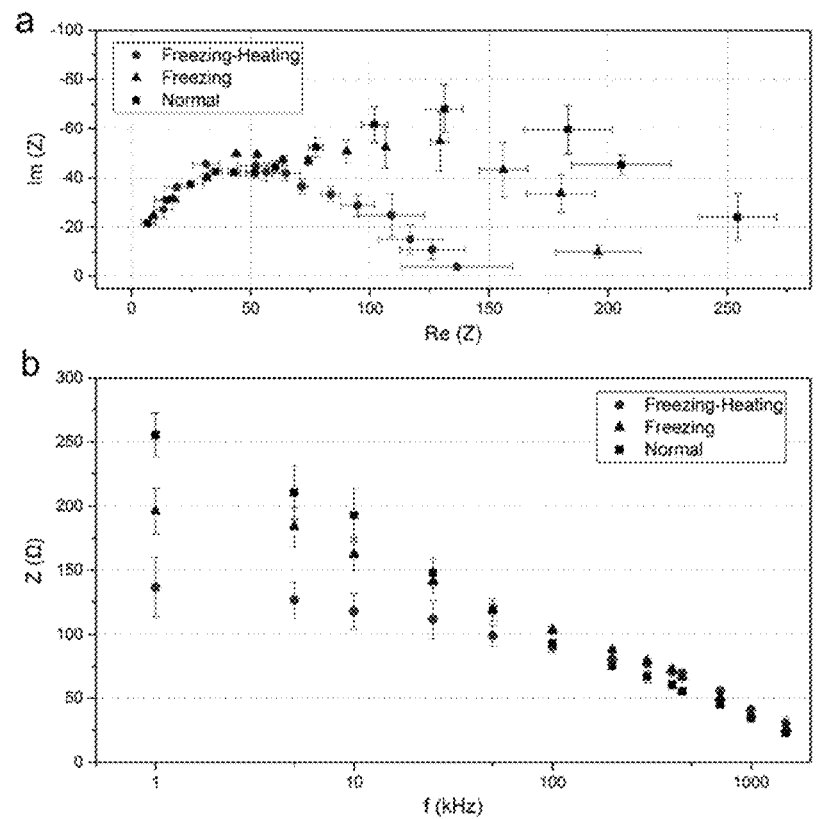
FIG. 6 is the measurement result of electrical impedance in an embodiment of the present application.

In FIG. 6a, the impedance $Z(\omega)$ measured under three different conditions (normal, pre-freezing and heating after pre-frozen) is plotted as a Cole-Cole curve, wherein the horizontal coordinate is the real part of the impedance and the vertical coordinate is the imaginary part. From the rightmost data point to the leftmost data point, the applied frequency increases from 1 kHz to 2 MHz. At low frequency, the data points under the three conditions are far apart. As the frequency increases, these data points gradually converge. FIG. 6b shows the impedance modulus changes as varied frequency. At low frequency, the impedance modulus value of the group of heating after pre-frozen is much smaller than that of the other two groups. As the frequency increases, the impedance modulus decreases, and the gap between different conditions becomes smaller. When the frequency is greater than 100 kHz, the data gradually converges.

Figure 7:
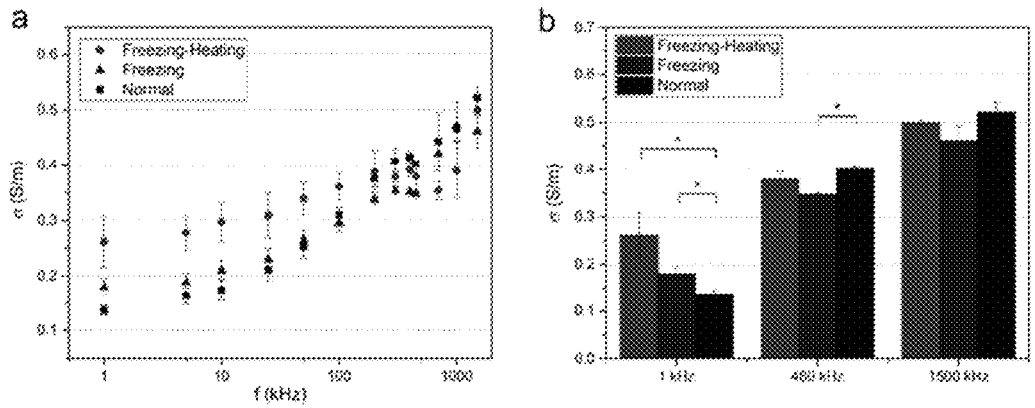
FIG. 7 is the result of change in conductivity with frequency in an embodiment of the present application.

Based on equations 1 and 3, calculating the tissue conductivity. FIG. 7a below shows the relationship between conductivity and frequency under three conditions. At low frequency, the conductivity of normal tissues is less than the conductivity of the other two conditions. As the frequency increases, the conductivity shows an upward trend, and the conductivity of normal tissues increases the most. Three representative frequencies of 1 kHz, 460 kHz and 1500 kHz are selected for analysis. As shown in FIG. 7b and Table 2 below, at 1 kHz, compared with normal tissue, the tissue conductivity of the group of heating after pre-frozen almost doubled compared with normal tissue, and there is a significant difference (P<0.05).

TABLE 2

| Electrical conductivity at three selected frequencies | | | |
|---|---|---|---|
| Electrical conductivity (S/m) | Normal | Freezing | Freezing-heating |
| 1 kHz | 0.137 ± 0.0088 | 0.179 ± 0.0166 | 0.262 ± 0.0464 |
| 460 kHz | 0.402 ± 0.0031 | 0.348 ± 0.0032 | 0.380 ± 0.0169 |
| 1500 kHz | 0.522 ± 0.0192 | 0.462 ± 0.0293 | 0.500 ± 0.0040 |

It can be seen from the above experimental results that the physical properties (conductivity) of different conditions (normal, pre-freezing and heating after pre-frozen) are different. The tissue conductivity has a great influence on RF heating. Therefore, by calculating the degree of change in the physical properties of the tissue during the pre-freezing process, the heating effect during the heating process can be accurately calculated.

The experimental verification results in an embodiment of this application are described below 1. Multimodal Ablation Experiment First, in-vitro and in-vivo experiments are conducted to compare temperature rise during radio frequency heating. Three pieces of fresh pork liver are used for vitro experiments. In each pork liver, two positions close to the center but not affecting each other are selected for two different types of RF heating: (a) direct RF heating; (b) RF heating after pre-frozen. The experiment uses a commercial RF bipolar probe (Olympus-CELON) for heating, and the effective length of the electrode is 2 cm. For the direct RF heating process, four thermocouples are used to record the temperature at different positions in the tissue. In order to determine the relative position among the thermocouples and the RF probe, here designs and manufactures a fixture with channels. The middle channel is used to fix the RF probe, and the remaining channels are used to fix the thermocouples. The four thermocouples are 4 mm, 5 mm, 8 mm and 10 mm from the RF probe. The insertion depth of the RF probe is 2 cm, the applied voltage is 460 kHz-30V, and the heating time is 3 minutes. For pre-freezing and then RF heating, the liver is first frozen using a laboratory-made freezing system. The diameter of the tip of the cryoprobe is 10 mm, and it closely fits the surface of the liver. Liquid nitrogen is flowing from the atmospheric liquid nitrogen tank to the freezing probe through a vacuum pump. The pump power is stabilized at 15 W to maintain a constant liquid nitrogen rate. The temperature of the probe surface in contact with the tissue will be measured by the thermocouples located in between. When the diameter of the ice ball on the tissue surface reaches 2.5 cm, ending freezing, and the total freezing time is about 8 minutes. After freezing, a thawing time of 15 minutes to ensure that the tissue returns to normal temperature. Subsequently, the RF probe and thermocouples are inserted into the center of the pre-frozen volume, and then the RF heating process is performed.

Three rabbits are used for in vivo experiments. The weight of the rabbits is between 2 kg-3 kg. First, anesthetize with intravenous injection of 1 ml/kg of 3% pentobarbital sodium solution. In the experiment, the rabbits are lying on their back and make a laparotomy to expose their livers. A rabbit has three-lobed livers in total, and the two lobed livers that are most likely to be exposed in each rabbit are selected for the experiment. Direct radio frequency heating and radio frequency heating after pre-frozen are performed in the two lobe livers, respectively. In order to avoid liver dehydration and carbonization, the voltage applied to the RF probe is set at 28.5V, and the remaining schemes are the same as the above-mentioned in vitro experiments.

Figure 8:
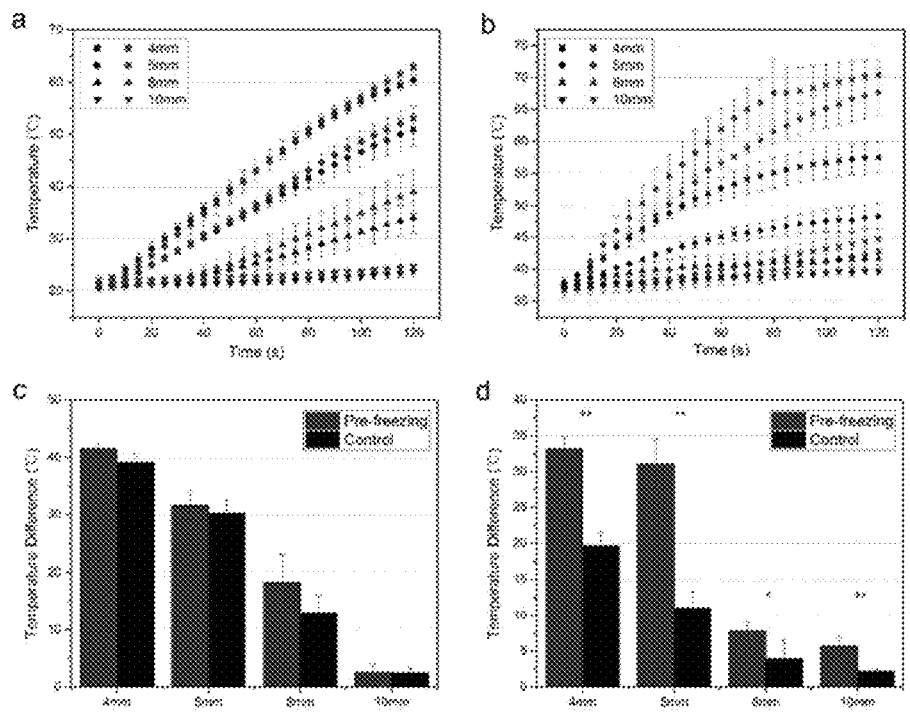
FIG. 8 is a multimodal ablation temperature field distribution diagram in an embodiment of the present application.

2. Multimodal Ablation of the Tissue Greatly Improves the Efficiency of Radiofrequency Ablation Experiments of radiofrequency heating directly and after pre-frozen are performed in the liver tissue. During the freezing process, the thermocouples record a minimum temperature of −110° C. on the surface of the freezing probe. FIGS. 8a and 8b show the temperature change curves of the RF heating process in vitro and in vivo, respectively. The red mark represents the group of RF heating after pre-frozen, and the black mark represents the group of direct RF heating. In-vivo experiments (FIG. 8b), the results show that the temperature of the pre-frozen tissue is significantly higher than that of the non-pre-frozen tissue: at 2 minutes, the maximum temperature of RF heating after pre-frozen exceeds 70° C., without pre-frozen RF heating, the maximum temperature is below 60° C. Under both conditions, there is a significant difference in the temperature increase range at each measurement point ($P<0.05$), proving that multimodal ablation greatly improving the efficiency of RF heating.

3. Multimodal Ablation Implements In-Situ Disruption of Cells and Microvessels, and Releases Active Antigen After the experiment, the rabbits are euthanized and the liver is removed. The ablated volume is excised from the liver and fixed with 10% neutral formalin solution. After fixed, each sample is divided into two along the central cross section (perpendicular to the RF probe). After embedding the samples in paraffin, tissue sections are taken, and then HE staining is used to scan with an optical microscope. FIG. 9 shows the histopathological images of direct radiofrequency heating (a-d) and radiofrequency heating (e-h) after tissue freezing. Around the needle track of the RF needle (hollow in FIG. 9a), the obvious thermal damage volume can be seen under both conditions. In FIGS. 9a and 9e, H1 and H2 show two different ablation volumes, and H3 volume is peripheral normal tissue. In the central volume of ablation (H1 volume) (FIG. 9b and FIG. 9f), the nucleus of most cells is constricted, and the cytoplasm shows contraction zone necrosis or coagulation necrosis. the bandwidth is relatively consistent under the two conditions, which are 2.173±0.198 mm and 2.674±0.043 mm, respectively. However, there is a transition volume (H2 volume) outside the central coagulation volume. In this volume, tissue cells and blood vessels are largely disrupted, and the nucleus is also constricted. Compared with direct radiofrequency heating, the bandwidth of the H2 volume radiofrequency heating after tissue pre-frozen is greatly increased (3.129±0.113 mm compared with 0.483±0.117 mm), and the bleeding is more serious and the cell disruption is more thorough. This phenomenon not only proves that the volume of multimodal ablation increases significantly under the same heating power, but also that in-situ cell disruption at sub-high temperature releases a large amount of active antigen, which can activate the body's immune response.

This experimental result proves that the effect of heating treatment under different physical properties will be very different, and through the preoperative planning of this application, the degree of property changes in the pre-freezing process can be calculated more accurately, and the property changes caused by further heating on this property changes result, so that the treatment results under a specific plan can be predicted more accurately, or the required plan can be calculated according to the required treatment results.

Each method implementation of the present invention can be implemented in software, hardware, firmware, and so on. Regardless of whether the invention is implemented in software, hardware, or firmware, the instruction code can be stored in any type of computer-accessible memory (e.g., permanent or modifiable, volatile or non-volatile, solid-state or non-solid, fixed or replaceable media, and so on). Similarly, the memory may be, for example, Programmable Array Logic ("PAL"), Random Access Memory ("RAM"), Programmable Read Only Memory ("PROM"), Read-Only Memory ("ROM"), Electrically Erasable Programmable ROM ("EEPROM"), magnetic disks, CDs, and Digital Versatile Discs ("DVD") and so on.

Embodiments of the present invention further comprise a computer system comprising a processor and a storage medium, wherein the storage medium stores a program for implementing the above method embodiment, and the processor is used to execute the program to implement the technical solution described in the above method implementation.

It should be noted that those skilled in the art should understand that the implementation functions of the modules shown in the embodiments of the above preoperative planning apparatus for multimodal ablation treatment can be referred to the relevant description of the foregoing preoperative planning method for multimodal ablation treatment to understand. The functions of each module shown in the above embodiments of the preoperative planning apparatus for multimodal ablation treatment can be implemented by a program (executable instructions) running on the processor, or by a specific logic circuit. If the user equipment described above is implemented in the form of a software function module and sold or used as an independent product, it may also be stored in a computer readable storage medium. Based on this understanding, the technical solutions of the embodiments of the present invention can be embodied in the form of software products in essence or part of contributions to the prior art. The computer software product is stored in a storage medium, and includes several instructions to enable a computer device (which may be a personal computer, server, or network device, and so on) to perform all or part of the methods described in the embodiments of the present invention. The foregoing storage media include various media that can store program codes, such as a U disk, a mobile hard disk, a read-only memory (ROM, Read Only Memory), a magnetic disk, or an optical disk. In this way, the embodiments of the present invention are not limited to any specific combination of hardware and software.

Correspondingly, the embodiments of the present invention also provide a computer storage medium in which computer executable instructions are stored. When the computer executable instructions are executed by a processor, the method embodiments of the present invention are implemented.

In addition, an embodiment of the present invention also provides a preoperative planning apparatus for multimodal ablation treatment, which comprising a memory for storing computer executable instructions, and a processor; the processor is used to execute the computer executable in the memory to implement the steps in the above method embodiments.

It should be noted that in the application documents of the present patent, relational terms such as first and second, and so on are only configured to distinguish one entity or operation from another entity or operation, and do not necessarily require or imply any such actual relationship or order between these entities or operations. Furthermore, the term "comprises" or "comprising" or "includes" or any other variations thereof is intended to encompass a non-exclusive inclusion, such that a process, method, article, or device that comprises a plurality of elements includes not only those elements but also Other elements, or elements that are inherent to such a process, method, item, or device. Without more restrictions, the element defined by the phrase "include one" does not exclude that there are other identical elements in the process, method, article or equipment that includes the element. In the application file of this patent, if it is mentioned that an action is performed according to an element, it means the meaning of performing the action at least according to the element, and includes two cases: the behavior is performed only on the basis of the element, and the behavior is performed based on the element and other elements. Multiple, repeatedly, various, etc., expressions include 2, twice, 2 types, and 2 or more, twice or more, and 2 types or more types.

All documents referred to in this application are considered to be included in the disclosure of the present application as a whole, so as to serve as a basis for modification as necessary. In addition, it should be understood that various changes and modifications may be made by those skilled in the art after reading the above disclosure of the present application.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

What is claimed is:

1. A preoperative planning method for multimodal ablation treatment, comprising:
    acquiring, by one or more processors via an input device, one or more parameters of a volume to be ablated, wherein the volume to be ablated comprises a tumor;
    calculating, by the one or more processors, a freezing dosage required for effecting one or more first property changes to tissue within the volume according to both mechanical and biological effect of the freezing on the tissue within the volume and the one or more parameters of the volume to be ablated;
    acquiring, by the one or more processors, a first planning data required for the one or more first property changes to the tissue within the volume to satisfy a first predetermined condition;
    calculating, by the one or more processors, based on coupling of electromagnetic field and temperature field and taking into account the first property changes to the tissue within the volume after freezing and a synergy among treatment needles, a corresponding heating rate and total thermal dose required for in-situ disruption of all cells and/or microvessels within a boundary of the tumor to maximize release of tumor antigens and stimulate the body's immune response based on the principle of biological heat and mass transfer and thermal energy induced biological effect;
    acquiring, by the one or more processors, a second planning data required for one or more second property changes to the tissue within the volume caused by heating of the tissue within the volume to satisfy a second predetermined condition; and
    outputting, by the one or more processors, the first planning data and the second planning data.

2. The preoperative planning method for multimodal ablation treatment according to claim 1, wherein the outputting of the first planning data and the second planning data, comprises:
    displaying, on a display, a needle insertion scheme for the multimodal ablation and/or resulting temperature field distribution in form of text and/or graphics according to the first planning data and the second planning data.

3. The preoperative planning method for multimodal ablation treatment according to claim 1, wherein the first predetermined condition is that the properties of the tissue within the volume reach a state capable of uniformly conducting heat in all directions.

4. The preoperative planning method for multimodal ablation treatment according to claim 3, wherein the properties of the tissue within the volume reach a state capable of uniformly conducting heat in all directions, comprises that an ice ball is formed in the volume to be ablated, and the ice ball covers the entire volume to be ablated.

5. The preoperative planning method for multimodal ablation treatment according to claim 1, wherein the one or more first and second property changes comprise one or any combination of the following change: change in electrical conductivity, change in thermal conductivity, change in electrolyte distribution, change in blood flow distribution.

6. The preoperative planning method for multimodal ablation treatment according to claim 1, wherein the first planning data comprises one or any combination of the following:
    patient posture, skin puncture point, number of treatment needles, position of treatment needles, insertion path of treatment needles, number and distance of treatment needles withdrawal, freezing power and time, freezing rate.

7. The preoperative planning method for multimodal ablation treatment according to claim 1, wherein the second planning data comprises one or any combination of the following:
    patient posture, skin puncture point, number of treatment needles, position of treatment needles, insertion path of treatment needles, number and distance of treatment needles withdrawal, heating power and time, heating rate.

8. The preoperative planning method for multimodal ablation treatment according to claim 1, wherein the one or more parameters of the volume to be ablated comprise one or any combination of the following:
    the size, shape, relative position and tissue property information of the tumor and other tissues and organs in the volume to be ablated, the blood vessel distribution and the blood perfusion situation of the surrounding tissues.

9. The preoperative planning method for multimodal ablation treatment according to claim 8, wherein the acquiring parameters of the volume to be ablated, comprises,
    performing reconstruction and segmentation according to a patient's preoperative 2D or 3D images, and extracting the size, shape, relative position and tissue property information of the tumor and other tissues and organs;
    acquiring the blood vessel distribution and the blood perfusion of the tumor and surrounding tissues by imaging methods.

10. The preoperative planning method for multimodal ablation treatment according to claim 1, wherein the calculating freezing dosage further comprises: calculating, considering the influence of the tissue within the volume, large blood vessels, and blood flow, the number of freezing needles required for tissue pretreatment and the synergy among the freezing needles to ensure that the ice ball covers the entire tumor; and calculating a freezing rate of forming the ice ball and setting the freezing power.

11. The preoperative planning method for multimodal ablation treatment according to claim 1, wherein the calculating the freezing dosage comprises acquiring the one or more first property changes of the tissue in the volume after freezing by calculating a freezing range and the temperature field.

12. The preoperative planning method for multimodal ablation treatment according to claim 1, wherein the calculating corresponding heating rate and total thermal dose required for in-situ disruption of all cells and/or microvessels within the tumor boundary is followed by:
    changing a number and position distribution of the treatment needles, to ensure that the overlap degree between a heating range of the treatment needles and a freezing range of the treatment needles satisfies predetermined requirements.

13. The preoperative planning method for multimodal ablation treatment according to claim 1, wherein after the step of outputting the first planning data and the second planning data, further comprising:
    acquiring medical images of pre-inserted treatment needles;
    calculating the number and position of the pre-inserted treatment needles according to the medical images of the pre-inserted treatment needles;
    determining whether the number and position of the pre-inserted treatment needles are consistent with the first planning data and the second planning data;
    if inconsistent, according to the number and position of the pre-inserted treatment needles, simulating the temperature field distribution of the tumor cells and action of mechanical force, calculating ablation volume formed by the pre-inserted needles, and revising planning parameters according to the calculated ablation volume, including increasing or decreasing the number of treatment needles, adjusting position distribution of the treatment needles, increasing or decreasing the heating power and time.

14. The preoperative planning method for multimodal ablation treatment according to claim 13, wherein after revising the planning parameters according to the calculated ablation volume, further comprising:
    if the thermal dose generated according to the revised planning parameters is insufficient to cause in situ disruption of tumor cells and/or microvessels within the tumor boundary, then re-planning multimodal ablation plan and revising ablation strategy to ensure complete local ablation of the tumor in the volume to be ablated.

15. A preoperative planning apparatus for multimodal ablation treatment, comprising:
    a memory for storing computer executable instructions; and,
    a processor, configured to implement the steps of the preoperative planning method for multimodal ablation treatment according to claim 1 when executing the computer executable instructions.

16. A computer readable storage medium, wherein the computer readable storage medium stores computer executable commands, which are executed by a processor to implement the steps in the method according to claim 1.

* * * * *